United States Patent [19]

Hutson, Jr. et al.

[11] 4,276,439
[45] Jun. 30, 1981

[54] CATALYTIC ALKYLATION METHOD AND APPARATUS WITH HYDROCARBON RECYCLE

[75] Inventors: Thomas Hutson, Jr.; Donald J. Makovec; Alden E. Beckworth, all of Bartlesville, Okla.

[73] Assignee: Phillips Petroleum Company, Bartlesville, Okla.

[21] Appl. No.: 81,290

[22] Filed: Oct. 2, 1979

[51] Int. Cl.³ .............................................. C07C 3/54
[52] U.S. Cl. .................................... 585/720; 585/723
[58] Field of Search ............................... 585/720, 723

[56] References Cited

U.S. PATENT DOCUMENTS

| 3,080,438 | 3/1963 | Sailors | 585/701 |
| 3,190,935 | 6/1965 | Hutson | 585/867 |
| 3,213,157 | 10/1965 | Hays et al. | 585/703 |
| 3,233,007 | 2/1966 | Chapman | 585/720 |
| 3,435,092 | 3/1969 | Hutson et al. | 585/720 |
| 3,817,708 | 6/1974 | Vernon | 585/723 |
| 3,928,486 | 12/1975 | Sobel | 585/312 |
| 4,094,923 | 6/1978 | Dixon | 585/714 |
| 4,161,497 | 7/1979 | Makovec et al. | 585/714 |

*Primary Examiner*—Curtis R. Davis

[57] ABSTRACT

A process and apparatus for the catalytic alkylation of an isoparaffin with one or more olefins. Reactant hydrocarbons are passed in contact with a liquid catalyst such as hydrofluoric acid in a reaction zone. The hydrocarbon phase is allowed to separate from the catalyst phase in a settling zone, and a portion of the hydrocarbon phase is cooled and reintroduced to the reaction zone in a separate stream from that of the feed hydrocarbons. The alkylation apparatus by which the process is carried out includes a vertical reaction vessel, which in a preferred embodiment is 2 to 6 feet in height, a settling vessel, means for fluid flow from the reaction vessel to the settling vessel, a conduit for fluid flow between the upper part of the settling vessel and the reaction zone, and means for cooling fluid in this conduit.

13 Claims, 1 Drawing Figure

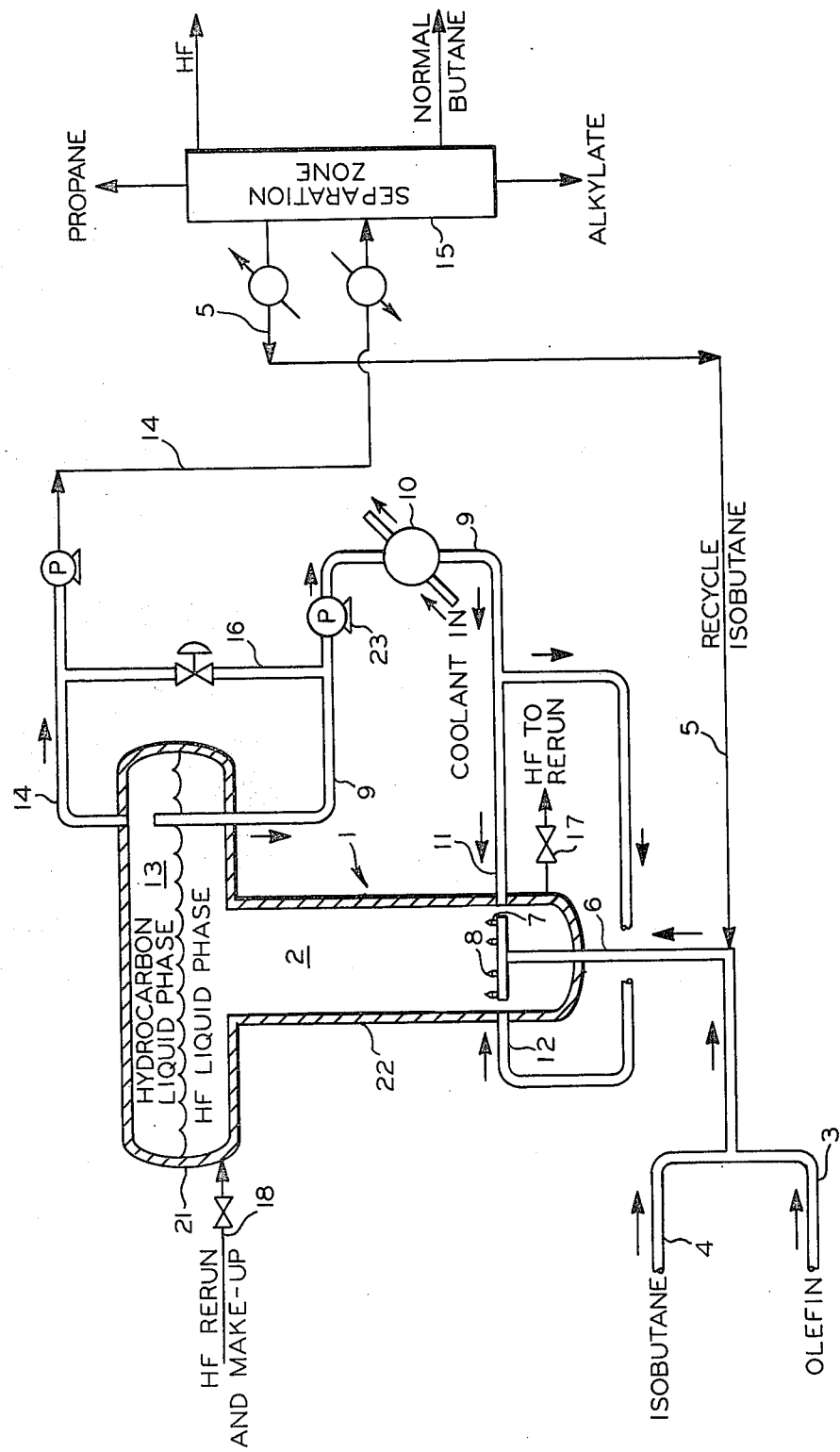

CATALYTIC ALKYLATION METHOD AND APPARATUS WITH HYDROCARBON RECYCLE

BACKGROUND OF THE INVENTION

This invention relates to the catalytic alkylation of an isoparaffin with one or more olefins. It further relates to apparatus for carrying out alkylation.

The catalytic alkylation of an isoparaffin with one or more olefins to produce a branched chain paraffin is a commercially important process for producing high-octane gasoline. Conventional catalytic alkylation processes generally involve the reaction of an isoparaffin such as isobutane with an olefin such as propylene and/or a butylene in the presence of a liquid alkylation catalyst, followed by the separation of the unreacted and product hydrocarbons from the catalyst in a settling zone and purification of the product alkylate. Because of the exothermic nature of the reaction, it is necessary to provide means of controlling the temperature inside the reaction vessel and maintaining the optimum alkylation temperature. Methods of maintaining this temperature include recycling the catalyst from the settling zone through a cooler and back to the reaction zone and recycling hydrocarbons from the settling zone through a cooler to be added to the hydrocarbon feed stream. Because of the corrosiveness of the catalysts used in alkylation, it is desirable to minimize catalyst circulation. It is also desirable to design the alkylation system so as to produce an alkylate which has a high octane rating.

Alkylation reaction apparatus known as open-pipe riser reactors comprise a vessel in which feed hydrocarbons are emulsified with liquid catalyst. The intimate contact between acid catalyst and hydrocarbons necessary for efficient reaction between olefin and paraffin is provided by injecting the hydrocarbons into the reactor through high-pressure nozzles in the form of a fine dispersion. Commercial open-pipe riser reactors are generally 20 to 40 feet in height and 2 to 4 feet in diameter. It is desirable in terms of economy and maintenance to reduce the size of commercial reactors and to minimize the flow of acid catalyst while maintaining the quality of the alkylate produced.

It is thus an object of this invention to provide an alkylation process and apparatus in which a high-octane alkylate is produced and acid circulation is minimized.

It is a further object of one aspect of the invention to provide relatively small alkylation apparatus.

SUMMARY OF THE INVENTION

According to the invention, an isoparaffin is alkylated with at least one olefin in the presence of an alkylation catalyst in a reaction zone, the reaction effluent separates into a hydrocarbon phase and a catalyst phase in a settling zone, and a portion of the hydrocarbon phase is cooled and introduced into the reaction zone separately from the hydrocarbon feed stream.

Further according to the invention, an alkylation riser reactor is provided which comprises a vertical reaction vessel, a settling vessel, means for fluid flow from the reaction vessel to the settling vessel, means for fluid flow between the upper part of the settling vessel and the reaction zone, and means for cooling the fluid in this conduit. In a preferred embodiment, the vertical portion of the reaction vessel is two to six feet in height and has an integral settling zone in a horizontal vessel openly connected to the upper portion of the vertical reactor.

BRIEF DESCRIPTION OF THE DRAWINGS

The FIGURE is a simplified schematic flow diagram of the invention process showing the preferred form of the alkylation apparatus.

DETAILED DESCRIPTION OF THE INVENTION

In the process of the invention, an isoparaffin is reacted with at least one olefin in the presence of a catalyst under conditions which maintain reactants and catalyst in the liquid phase. The isoparaffin can be any alkylatable isoparaffin such as isobutane or isopentane and the olefin can be a low molecular weight olefin such as propylene, a butylene, an amylene, and like hydrocarbons, or a mixture of these. The alkylation catalyst is generally an acid-acting liquid such as sulfuric acid, hydrogen fluoride, phosphoric acid, a halosulfonic acid and aluminum chloride. Hydrogen fluoride is the preferred catalyst because of its ability to be reused and because of the superior quality of the alkylate produced. The hydrogen fluoride catalyst used is generally 85 to 98 weight percent HF and 2 to 15 weight percent water, acid-soluble oils and hydrocarbons. The alkylates produced are branched paraffins, generally isomers of heptane, octane and like hydrocarbons.

The process of the invention can be described more fully by reference to the FIGURE, which illustrates an embodiment of the invention in which liquid isobutane is alkylated with a liquid mixture of propylene and butylenes in liquid hydrogen fluoride catalyst.

A stream of olefins 3 generally at about 80° F. or ambient temperature is mixed with a stream of feed or fresh isobutane 4 and a stream of recirculated isobutane 5, and the resulting combined feed stream 6 is divided into individual streams 7 and injected into reaction vessel 1 through high pressure nozzles 8. The feed mol ratio of isobutane to olefin (including both fresh isobutane and isobutane recirculated for addition to the feed stream) will generally be in the range 2:1 to 30:1, optimally for commercial operations about 10:1 to 12:1 for production of high-octane alkylate. The hydrocarbon stream is introduced directly into catalyst phase 2 in the form of a fine dispersion. The nozzle velocity, opening diameter and pressure drop across the nozzle determine droplet size and degree of dispersion. Depending upon the size of the reactor, the feed can be introduced through 1 to 200 nozzles each having an opening diameter of 0.01 to 0.60 inch. The pressure drop across each nozzle can vary from 20 to 100 psig, but is generally 24-45 psig, and nozzle velocity is within the range of about 10 to about 125 feet per second. The resulting hydrocarbon droplet size will generally be in the range of 10 to 1000 microns, preferably 10 to 100 microns to give good contact with the catalyst. The level of the catalyst above the nozzles and the fineness of the spray can be adjusted to give the residence time of reactants in the reaction zone which gives maximum octane value for the product. Although the residence time of hydrocarbons in the reaction zone can vary widely depending upon the variables discussed above, the practice of the invention in the preferred apparatus will permit residence times of 30 to 120 seconds, optimally about 80 seconds.

Pressure in the reaction zone will be about 120 to 200 psig, sufficient to maintain the reactants in the liquid phase.

The reacting hydrocarbons and reaction products rise in the reactor through the liquid catalyst. The reaction effluent containing hydrocarbons, fluorocarbons, and catalyst can be withdrawn from the upper portion of the vertical reactor and fed into a settling tank for separation of the hydrocarbon phase from the catalyst phase. In the embodiment illustrated in the FIGURE, the settling zone is located in the upper portion of the reactor, in a horizontally-elongated tank openly connected with the top of the vertical reaction zone. In this settling zone, the reaction effluent is continuously separated into an upper liquid hydrocarbon phase 13 comprising alkylation products and unreacted isoparaffin, and a lower liquid catalyst phase.

A portion of the hydrocarbon phase is passed via conduit 14 to a separation zone 15 where the product alkylate is separated from unreacted isobutane, normal butane, propane and catalyst. The separation of the components of the alkylate stream conventionally includes several fractionation steps. Isobutane recovered from the hydrocarbon stream is cooled and recycled in stream 5 to be combined with feed olefins and fresh isobutane for reintroduction into the reactor. It is within the scope of the invention to combine at least a portion of isobutane recycle stream 5 with the cooled hydrocarbon recycle stream 9 for direct injection into the reaction zone. This would require the decrease in nozzle orifice size to attain the same pressure drop across the feed hydrocarbon nozzles.

The portion of hydrocarbon phase 13 which is not fed to the fractionation zone for alkylate recovery is removed in stream 9, either directly from the settling zone or via 16 from hydrocarbon stream 14. Stream 9 is cooled in 10, which can be any conventional heat exchange unit such as a shell-tube heat exchanger, to about 80° F. or to the temperature necessary to maintain the optimum reaction temperature in the reaction zone. The cooled hydrocarbon stream is reintroduced into reactor 1 separately from the combined feed stream 6. In commercial operations, the inlet velocity of the recycled hydrocarbons will be about 0.1 to about 5 feet per second. There can be from 1 to about 20 inlets for recycled hydrocarbon, with each inlet opening being from 0.125 inch to about 6 inches in diameter. The FIGURE shows the recycled hydrocarbon stream divided into two streams 11 and 12, but the number of recycled hydrocarbon streams entering the reactor can vary widely depending upon the particular reaction conditions and the size of the reactor. The cooled hydrocarbon stream aids in maintaining the desired reaction temperature in the reactor, which is generally 70° to 90° F. but can range from 40° to 120° F., the higher temperatures generally applying to propylene alkylation. In the embodiment illustrated in FIG. 1, the hydrocarbon recycle streams are injected at right angles to the direction of injection of mixed feed stream 6. Each recycle stream is introduced into the reactor at approximately the same catalyst level as the level of introduction of the combined feed stream, the level of entry being within 12 inches above or below the catalyst level of the feed nozzle outlets. This hydrocarbon recycle stream contains predominantly isobutane, but also includes organic fluorides, propane, normal butane and alkylate. It is believed that, in the reaction zone, organic fluorides in this stream react with isobutane in the presence of hydrocarbon fluoride to produce additional alkylate, releasing HF in the process.

As needed to maintain catalyst concentration in the reactor, catalyst can be intermittently or continuously removed via 17 to a rerun unit (not shown) to remove acid-soluble oils and water by distillation. Rerun and/or makeup catalyst can be added to the reactor through 18. The catalyst bed is essentially static, i.e., there is no appreciable continuous external circulation of catalyst. It is known that in large-scale riser reactors there is a tendency of the catalyst to move down along the walls of the vessel, so that there is a form of internal circulation of catalyst upward with the reacting hydrocarbons and downward along the sides of the reactor.

The reactor which can be used in the practice of the process of the invention is shorter in height and larger in diameter relative to height than conventional alkylation riser reactors, which are generally about 40 feet in height and about 2.5 feet in diameter. The invention reactor can, for example, have a diameter to height ratio of about 1:14 to 1:1, although the actual dimensions may vary widely depending upon the other variables in the alkylation system. The height of the vertical portion of the vessel can range from 2 to 6 feet, and the diameter can be 0.14 to 5 feet.

The FIGURE also illustrates an embodiment of the alkylation reaction vessel of the invention. Reaction vessel 1 has a lower vertical portion 22 into which isobutane and olefins in combined feed stream 6 are injected through nozzles 8 having a nozzle velocity of about 50 feet per second. The nozzle for commercial operations can be any suitable nozzle which can produce a fine dispersion of hydrocarbon, such as Spraying Systems Company WhirlJet nozzle Type B having a 3/64 inch to ⅜ inch diameter orifice. The number of nozzles and orifice size used depends on the pressure drop across the nozzle desired, nozzle velocity desired and quantity of liquid charged to the reactor. Hydrocarbons recycled in line 9 according to the invention process are introduced into the lower portion of the reaction vessel. The hydrocarbons can be introduced through a nozzle or, as shown in the drawing, directly into the reactor through an opening in the reactor wall. In the illustrated embodiment, the introduction of the recycle stream into the catalyst is at right angles via lines 11 and 12 to the introduction of mixed feed stream 6 via nozzles 8. Separation of the lighter hydrocarbon phase from the denser acid phase takes place in the upper horizontal portion 21 of the reactor. The hydrocarbon phase can be removed through line 14 in the upper portion of horizontal settling zone 21. The recycle portion of the hydrocarbon phase can be removed in line 9 or, alternatively, in line 16. This recycle hydrocarbon stream is pumped by conventional pump 23 through heat exchanger 10 and back into the reaction vessel.

Table I presents process conditions and yields for a test run carried out according to the process of the invention. In this run, liquid isobutane was alkylated with liquid butylenes in liquid hydrogen fluoride catalyst. The reactor used for this test run was a small-scale experimental model of a riser reactor which was about 49 mm in diameter and about 700 mm in height. One nozzle for introduction of the combined feed stream was used. The opening diameter for this nozzle was 0.38 mm (0.015 inch) and the pressure drop across the nozzle was 37 psi (240 kPa). One lateral recycle hydrocarbon stream having an opening diameter of 9.3 mm (0.364 inch) was introduced at a point slightly below the level of the outlet of th feed nozzle.

TABLE I

| Operation: | |
|---|---|
| Feed Olefin, gallons/hr. | 0.062 |
| Composition, volume % | |
| Butene-1 | 22.4 |
| Isobutylene | 28.3 |
| Butenes-2 | 49.3 |
| Feed Isobutane, gallons/hr. | 0.258 |
| Composition, volume % | |
| Propane | 0.34 |
| Isobutane | 96.09 |
| Normal butane | 3.57 |
| Recycle Isobutane, gallons/hr. | 1.27 |
| Composition, volume % | |
| Propane | 0.66 |
| Isobutane | 98.76 |
| Normal butane | 0.58 |
| Recycle Hydrocarbon, gallons/hr. | 11.1 |
| Composition, volume % | |
| Propane | 0.65 |
| Isobutane | 91.64 |
| Normal butane | 1.17 |
| Pentane plus | 6.54 |
| HF Catalyst | |
| Volume, gallons | 0.75 |
| Composition, wt. % | |
| HF | 90.6 |
| $H_2O$ | 3.7 |
| Acid Soluble Oils | 0.2 |
| Hydrocarbons | 5.5 |
| Feed plus recycle isobutane/olefin mol ratio | 24:1 |
| Total IC$_4$/Olefins, Volume Ratio | 188:1 |
| Hydrocarbon Recycle/Olefins, Volume Ratio | 180:1 |
| Total of all Hydrocarbon/HF Catalyst Volume Ratio | 2.8:1 |
| Volume of Total Hydrocarbon per Volume of Catalyst/hr. | 17 |
| Reaction Temperature, °F. | 80 |
| Reaction Pressure, psig | 148 |
| Debutanized Alkylate | 96.0 (Research Octane, 0 cc TEL) |
| Nozzle Velocity (Combined feed stream), ft/sec | 50 |
| Orifice Velocity (Recycle hydrocarbon stream), ft/sec | 0.6 |

The following runs were performed in the test reactor and provide comparisons of the invention process with other alkylation processes. For those runs in which there was no hydrocarbon recycle, the acid catalyst was cooled and recycled to the reactor.

A run was performed using the mixed butylenes (butene-1, butene-2 and isobutene) of the invention run shown in Table I, except that cooled acid circulation from the settling zone to the reaction zone was substituted for cooled hydrocarbon recirculation. The RON clear (research octane number, 0 cc tetraethyl lead) of the alkylate produced in this run was about 94.9. An improvement of 1.1 octane numbers thus resulted from cooling the hydrocarbon stream and reintroducing it into the reaction zone, rather than using an acid cooling stream and no hydrocarbon recycle as in the comparative run.

Similar runs were performed with propylene using an isobutane-to-propylene feed ratio of 29:1. When the run was performed with no hydrocarbon recycle, the RON clear was about 91.25; with hydrocarbon recycle from the settling zone directly into the reaction zone, the RON clear value of the alkylate was about 91.65. While the practice of the invention thus resulted in an improvement in octane rating of the product, the advantage in terms of the octane of the alkylate was not as pronounced in the propylene run as in the butylene run described above.

Test runs were also performed in the experimental reactor using a 44/56 weight ratio mixture of propylene/butylenes. The isobutane-to-olefin feed ratio was 10.5/1. When this mixed olefin feed was charged to the reaction zone through the nozzle with no hydrocarbon recycle employed, the RON clear of the alkylate was about 92.8. When the run was repeated with a hydrocarbon recycle stream injected into the reaction zone through the nozzle, that is, combined and introduced as part of the feed stream (resulting in an isobutane-to-olefin ratio of 22:1), the alkylate produced had a RON clear octane number of 92.7. Similar runs were then performed using isobutane-to-olefin ratios of 6.7:1 (without hydrocarbon recycle) and 18.0:1 (with hydrocarbon recycle through the nozzle), with resulting alkylate octane numbers of 92.7 and 92.4, respectively. Because of the different olefin feed and the different isobutane-to-olefin ratios used in these mixed olefin runs as compared with the invention runs using butylenes and propylenes described above, no direct comparison of the runs was made. However, based on the data obtained for mixed olefins which shows that, in the test reactor employed and under the reaction conditions which existed, there was no improvement in octane number when the hydrocarbon phase was recycled through the feed nozzle as compared with when the hydrocarbon phase was not recycled at all, the inference can be drawn that hydrocarbon recycle directly into the reaction zone according to the invention represents an improvement over recycle to the feed stream and introduction into the reaction zone via the feed nozzle.

We claim:

1. An alkylation process comprising the steps of:
   (a) injecting a feed hydrocarbon stream comprising an isoparaffin and at least one olefin into an alkylation catalyst bed in an alkylation zone under conditions suitable for producing an alkylate, and producing an alkylation effluent comprising the alkylate and the alkylation catalyst;
   (b) passing the alkylation effluent to a phase separation zone and therein forming an upper liquid hydrocarbon phase comprising the alkylate and unreacted isoparaffin and a lower alkylation catalyst phase;
   (c) withdrawing, as a recycle hydrocarbon stream, a first portion of the liquid hydrocarbon phase from the phase separation zone, cooling the recycle hydrocarbon stream, passing the cooled recycle hydrocarbon stream to the alkylation zone, and injecting the cooled recycle hydrocarbon stream directly into the alkylation catalyst bed without prior contact with the feed hydrocarbon stream;
   (d) withdrawing, as a product stream, a second portion of the liquid hydrocarbon phase from the phase separation zone.

2. The alkylation process of claim 1 wherein the recycle hydrocarbon stream is injected into the alkylation catalyst in the reaction zone at approximately right angles to the direction of injection of the feed hydrocarbon stream.

3. The alkylation process of claim 1 further comprising the steps of (e) passing the product stream to a fractionation zone;
(f) separating the unreacted isoparaffin from the product stream in the fractionation zone; and
(g) passing the thus separated unreacted isoparaffin from the fractionation zone to the feed hydrocarbon stream and injecting the unreacted isoparaffin into the reaction zone as a constituent of the feed hydrocarbon stream.

4. The alkylation process of claim 3 wherein at least a portion of the unreacted isoparaffin separated from the product stream in step (f) is combined with the recycle hydrocarbon stream.

5. The alkylation process of claim 1 wherein the alkylation catalyst is liquid hydrogen fluoride and the alkylation catalyst bed is essentially static.

6. The alkylation process of claim 5 wherein the feed hydrocarbon stream is injected into the alkylation zone through at least one nozzle in the form of a fine dispersion.

7. The alkylation process of claim 6 having a hydrocarbon residence time in the alkylation zone of 30 seconds to 120 seconds.

8. The alkylation process of claim 6 wherein the recycle stream is introduced into the reaction zone at a level in the alkylation catalyst which is within 12 inches above or below the level in the alkylation catalyst of the at least one nozzle.

9. The alkylation process of claim 1, claim 5 or claim 8 wherein the isoparaffin is selected from the group consisting of isobutane and isopentane and the olefin is selected from the group consisting of ethylene, propylene, isobutene and mixtures thereof.

10. The alkylation process of claim 9 wherein the isoparaffin is isobutane and the olefin is selected from butene-1, butene-2, isobutylene, and mixtures of these.

11. The alkylation process of claim 10 wherein the reaction is carried out under a temperature of 40° to 110° F. and a pressure of 120 to 200 psig.

12. The alkylation process of claim 11 wherein the reaction temperature is maintained within the range of 70° to 90° F.

13. The alkylation process of claim 12 in which the liquid hydrocarbon phase further comprises organic fluorides.

* * * * *